United States Patent
Cochran

(10) Patent No.: US 11,724,436 B2
(45) Date of Patent: Aug. 15, 2023

(54) NASAL CAST BENDER

(71) Applicant: Spencer Cochran, Dalls, TX (US)

(72) Inventor: Spencer Cochran, Dalls, TX (US)

( * ) Notice: Subject to any disclaimer, the term of this patent is extended or adjusted under 35 U.S.C. 154(b) by 605 days.

(21) Appl. No.: 15/625,455

(22) Filed: Jun. 16, 2017

(65) Prior Publication Data

US 2018/0361649 A1  Dec. 20, 2018

(51) Int. Cl.
| | | |
|---|---|---|
| B29C 53/02 | (2006.01) | |
| A61F 5/08 | (2006.01) | |
| A61F 13/12 | (2006.01) | |
| A61F 13/00 | (2006.01) | |
| B29L 31/00 | (2006.01) | |

(52) U.S. Cl.
CPC .............. B29C 53/02 (2013.01); A61F 5/08 (2013.01); A61F 13/126 (2013.01); A61F 2013/00578 (2013.01); A61F 2013/00625 (2013.01); A61F 2013/00817 (2013.01); B29L 2031/753 (2013.01)

(58) Field of Classification Search
CPC ......... B29C 53/02; B29C 53/00; B29C 53/04; B29C 53/46; B29C 53/52; B29C 53/72; B29C 53/82; A61F 5/08; A61F 13/126; A61F 2013/00476; A61F 2013/00578; A61F 2013/00625; A61F 2013/00817; A61B 2017/00792; A61B 17/02; A61B 17/0206; A61B 17/0281; A61B 1/32; B29L 2031/753

See application file for complete search history.

(56) References Cited

U.S. PATENT DOCUMENTS

| | | | | |
|---|---|---|---|---|
| 605,715 | A * | 6/1898 | Hohmann | A61B 17/02 600/219 |
| 3,542,015 | A * | 11/1970 | Steinman | A61B 17/02 600/206 |
| 3,594,813 | A * | 7/1971 | Sanderson | A61F 13/126 128/857 |
| 3,742,943 | A * | 7/1973 | Malmin | A61F 5/08 606/204.45 |
| 5,971,763 | A * | 10/1999 | Yau | A45D 44/14 434/377 |
| 6,428,472 | B1 * | 8/2002 | Haas | A61B 17/02 600/206 |

(Continued)

FOREIGN PATENT DOCUMENTS

KR  101634375 B1 *  6/2016

OTHER PUBLICATIONS

Dialog Machine Translation of KR-101634375-B1; "KR_101634375_B1_eng_and_kr.pdf".*

(Continued)

*Primary Examiner* — Rachael E Bredefeld
*Assistant Examiner* — Seth R. Brown
(74) *Attorney, Agent, or Firm* — Andrew M. Metrailer; Conley Rose, P.C.

(57) ABSTRACT

Embodiments relate generally to systems and methods for shaping an external nasal cast. A nasal cast bender may comprise a base; and a protrusion protruding upwards from the base portion, wherein the protrusion comprises a handle and a bending surface comprising a convex profile; wherein the bending surface is configured to shape an external nasal cast.

20 Claims, 4 Drawing Sheets

(56) References Cited

U.S. PATENT DOCUMENTS

| | | | | |
|---|---|---|---|---|
| 7,117,543 | B1* | 10/2006 | Gunnarshaug | A61F 13/126 128/857 |
| 8,801,986 | B2* | 8/2014 | Matsui | B29C 64/165 434/270 |
| 2009/0267261 | A1* | 10/2009 | Mark | A61M 16/06 264/222 |
| 2012/0078367 | A1* | 3/2012 | Hristov | A61F 2/186 623/10 |
| 2016/0374846 | A1* | 12/2016 | Valinia | G09B 23/30 606/204.45 |

OTHER PUBLICATIONS

DuPont Performance Materials extrinsic evidence; "20210427_DuPontPerformanceMaterials_Delrin_POM.pdf".*

* cited by examiner

NASAL CAST BENDER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

During rhinoplasty, a surgeon may make incisions within each nostril and/or the base of the nose in order to separate nasal skin and/or soft tissue from the osseous and cartilaginous structures. The surgeon may then pull back or peel the nasal skin and/or soft tissue away from the osseous and cartilaginous structures and towards the patient's forehead. A surgical assistant may hold this nasal skin and/or soft tissue back, while the surgeon reshapes the osseous and cartilaginous structures, as desired. After the reshaping, the nasal skin and/or the soft tissue may be pulled over the osseous and cartilaginous structures, and the incisions may be sutured. Then, the surgeon may apply an external nasal cast to the nose in order for the osseous and cartilaginous structures to heal in their reshaped position. The external nasal cast may be molded to the shape of the reconstructed nose to allow the reconstructed nose to heal in a correct/desired position. The shape and the positioning of the external nasal cast is visually controlled by the surgeon; that is, there is no standard device to examine a correctness of the shape and positioning of the external nasal cast. A crooked or undesirable nose due to the surgeon's decisions for shaping and positioning the external nasal cast may lead to an unsatisfied patient.

SUMMARY

In an embodiment, a nasal cast bender may comprise a base; and a protrusion protruding upwards from the base portion, wherein the protrusion comprises a handle and a bending surface comprising a convex profile; wherein the bending surface is configured to shape an external nasal cast.

In an embodiment, a nasal cast bender may comprise a base; a protrusion protruding upwards from the base portion, wherein the protrusion comprises a handle and a bending surface comprising a convex profile; and a line extending from the base to a hook; wherein the bending surface is configured to shape an external nasal cast.

In an embodiment, a method for shaping an external nasal cast, the method may comprise providing a nasal cast bender, wherein the nasal cast bender comprises: a base; and a protrusion protruding upwards from the base portion, wherein the protrusion comprises a handle and a bending surface comprising a convex profile; bending, sliding, and/or pressing the external nasal cast along the bending surface, thereby shaping the external nasal cast.

In an embodiment, a method for retracting nasal skin and/or soft tissue, the method may comprise providing a nasal cast bender, wherein the nasal cast bender comprises: a base; a protrusion protruding upwards from the base portion, wherein the protrusion comprises a handle and a bending surface comprising a convex profile; and a line extending from the base to a hook; making incisions within each nostril and/or a base of a nose; separating the nasal skin and/or the soft tissue from osseous and cartilaginous structures; attaching the hook to the nasal skin and/or the soft tissue; peeling the nasal skin and/or the soft tissue towards a forehead of a patient; traversing the forehead with the line; and suspending the nasal cast bender below the head of the patient with the line, thereby retracting the nasal skin and/or the soft tissue.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
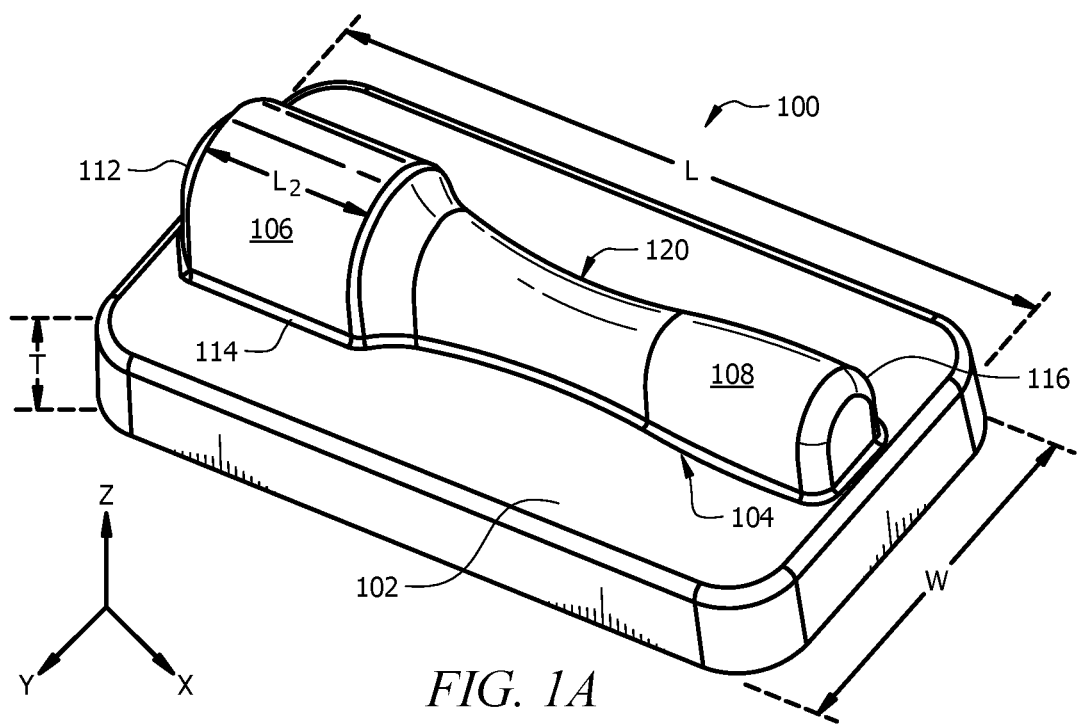
FIGS. 1A and 1B are schematic illustrations of a nasal cast bender in accordance with embodiments of the disclosure where contour lines are included for reference.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The disclosure may relate to a nasal cast bender. The nasal cast bender may shape an external nasal cast to conform to a patient's reconstructed (reshaped) nose in order to maintain and secure the shape of the patient's reconstructed nose. The external nasal cast may be made from a deformable material, such as, for example, plastic (e.g., thermoplastic), metal (e.g., aluminum), or combinations thereof. The external nasal cast may also be referred to as a nasal splint or nasal dressing.

The nasal cast bender may allow the external nasal cast to be shaped symmetrically, thereby allowing the reconstructed nose to heal symmetrically, once placed on the patient's reconstructed nose. Also, the nasal cast bender may allow a surgeon to symmetrically shape the external nasal cast while the external nasal cast is not on the patient's reconstructed nose, as opposed to shaping the external nasal cast while it is on the patient's reconstructed nose; this may prevent any shifting and/or damage to the reconstructed nose. The nasal cast bender may also be utilized as a weighted retractor for retracting nasal skin and/or soft tissue. The nasal cast bender may be sterilized via autoclaving.

FIG. 1A is a schematic illustration of nasal cast bender 100. In general, the nasal cast bender 100 serves to provide a variable surface upon which to form the nasal cast. The nasal cast bender 100 can include a base 102 and a handle 106 and bending surface 108 protruding from the base 102. The base serves to provide a flat and stable base for the nasal cast bender 100 during use. The handle 106 can serve to provide a gripping point for the nasal cast bender 100 while forming the nasal cast. The bending surface 108 can provide a variably shaped surface to allow a nasal cast to be shaped into a variety of forms having potentially different diameters to fit various patients having different sized and shaped noses after surgery. In this regard, a variety of shapes are possible for the bending surface 108.

The base 102 may be of any suitable shape, such as, for example, rectangular, circular, triangular, or combinations thereof. Base 102 may have a thickness, T, from about 0.5 inch to about 1.5 inches; a length, L, from about 4 inches to about 10 inches; a width, W, from about 3 inches to about 5 inches; and a weight from about 1 ounce to about 16 ounces. In some embodiments, the base 102 may be configured to stabilize nasal cast bender 100 during shaping of an external nasal cast. The bottom surface of the base 102 may generally form a flat surface, and the bottom surface can be solid or have one or more support features in alignment to form a flat base. In some embodiments, the corners of the base can be rounded or smoothed.

The protrusion 104 may include the handle 106 and the bending surface 108. The protrusion 104 may extend upwards from base 102, and extend along the length, L, of base 102.

Figure 2:
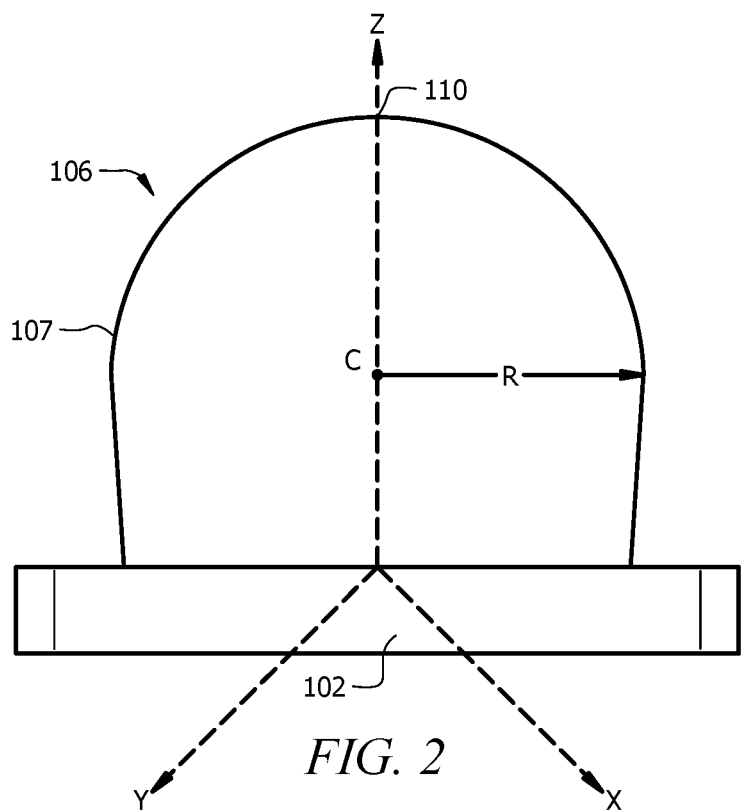
FIG. 2 illustrates a cross-section of a nasal cast bender in accordance with embodiments of the disclosure.

As shown on a cross-section of the nasal cast bender 100 depicted on FIG. 2, the handle 106 may include a convex profile that may resemble an upside down "U" protruding outward from base 102, and having an apex 110 of handle 106 over the base 102. A radius, R, of the handle 106 may extend from the center, C, of the handle 106 to the surface 107 of the handle 106. The radius R may vary along the surface 107 (e.g., radius may be from about 0.5 inch to about 2 inches) due to the varying profile (e.g., having a convex profiles, a concave profiles, etc.). The handle 106 may be symmetrical relative to vertical axis, z, extending from apex 110, through C, and to base 102.

With reference back to FIG. 1A, the handle 106 may extend along a length, $L_2$, of the handle 106 from the handle first end 112 to the handle second end 114. The handle 106 may be grasped by a user (e.g., a surgeon) for stability as the user shapes an external nasal cast by contacting (e.g., pressing, sliding, and/or bending) the external nasal cast along bending surface 108.

While shown in FIG. 1A as a rounded handle formed in the center of the base 102, the handle 106 can take a variety of forms. In some embodiments, the handle 106 can comprise any shape sufficient to provide a grasping surface to allow the nasal cast bender 100 to be retained in place while forming the bent nasal cast. For example, the handle 106 could take the form of a half circle, a knob, a ball, or the like. In some embodiments, the handle 106 and the bending surface 108 may be shaped to represent a generic forehead and nose of a patient, such that the handle 106 can comprise a partially rounded surface shaped like a forehead.

The bending surface 108 may extend from the handle second end 114 to the bending surface end 116. The bending surface 108 may have a smooth texture for shaping an external nasal cast. That is, the smooth texture may allow a user of the nasal cast bender 100 to slide, press, and/or bend the external nasal cast along the bending surface 108, thereby shaping the external nasal cast.

Figure 3:
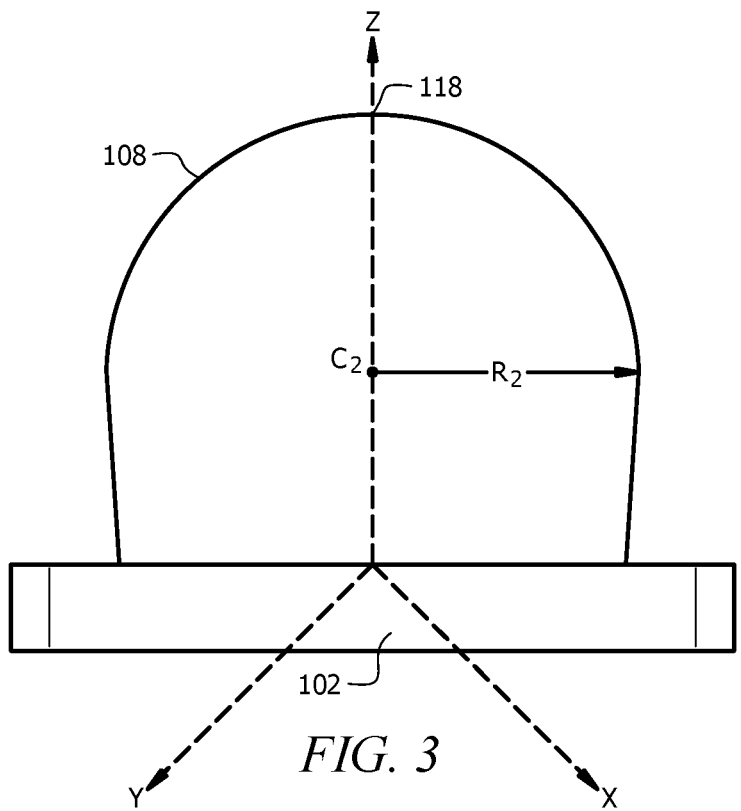
FIG. 3 illustrates another cross-section of a nasal cast bender in accordance with embodiments of the disclosure.

As shown on another cross-section of the nasal cast bender 100 depicted on FIG. 3, the bending surface 108 may include a convex profile that may resemble an upside down "U" protruding outward from base 102, with an apex 118 of the bending surface 108 above the base 102. A radius, $R_2$, of the bending surface 108 may extend from the center, $C_2$, of the bending surface 108 to the edge of the bending surface 108. The radius $R_2$ may vary along bending surface 108 (e.g., radius may be from about 0.125 inch to about 0.5 inch) due to the varying profile. The bending surface 108 may be tapered, where the radius $R_2$ may decrease from the handle second end 114 to the midpoint 120 of the protrusion 104. The radius $R_2$ may increase from the midpoint 120 to the bending surface end 116. That is, the radius $R_2$ may be the smallest at midpoint 120. The tapering may allow for a user to vary a shape and/or degree of bending of an external nasal cast, as the user presses, slides and/or bends the external nasal cast along bending surface 108. The bending surface 108 may be symmetrical relative to vertical axis, z, extending from apex 118, through the center $C_2$, and to the base 102. A circumference of the handle 106 may be greater than a circumference of the bending surface 108. Also, the radius R may be greater than or equal to the radius $R_2$.

While shown as having a convex shape in FIG. 1A, the bending surface 108 may also have a straight (e.g., conical) or concave shape along the length L of the nasal cast bender 100. In some embodiments, the bending surface 108 may have a varying radius along its length so that a varying radius is present to allow for the formation of a bent cast having a bend that matches a patient's nose, which can vary from patient to patient. In some embodiments, all or portions of the bending surface may have a constant radius along the length L.

Figure 1B:
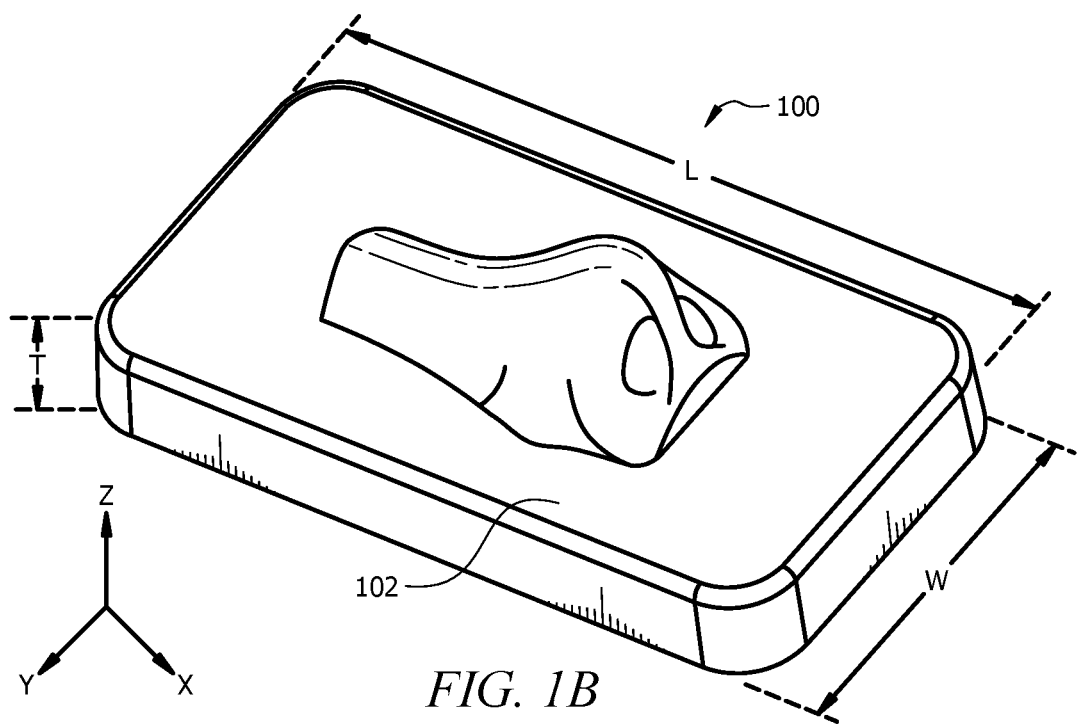

In some embodiments as shown in FIG. 1B, the bending surface 108 can be shaped to represent a nose, which can be stretched and/or exaggerated in order to provide a varying bending surface. The nose can be symmetric in order to aid in forming a symmetrically bent nasal cast. The use of a bending surface 108 in the shape of a nose may help to provide a guide during the bending of the cast to be able to match the size and shape of a patient's nose on the nasal cast bender prior to placement of the bent cast on the patient. As shown in FIG. 1B, the cast bender may or may not have a handle portion in various embodiments.

Nasal cast bender 100 may be made from any suitable material. In some embodiments, the nasal cast bender 100 may be formed of a material that can be autoclaved, and may comprise a relatively non-porous smooth surface to provide a sterilized surface. For example, the nasal cast bender 100 can be formed from a material such as, for example, plastic, metal (e.g., aluminum), or combinations thereof. In some embodiments, the nasal cast bender 100 may be a single piece, integrated component that can be created by injection molding, forming, printing (e.g., using a 3D printer) or the like. In some embodiments, the nasal cast bender may be solid or hollow, where the choice of construction can depend on the desired final weight, size, and material of construction of the nasal cast bender 100.

Figure 4:
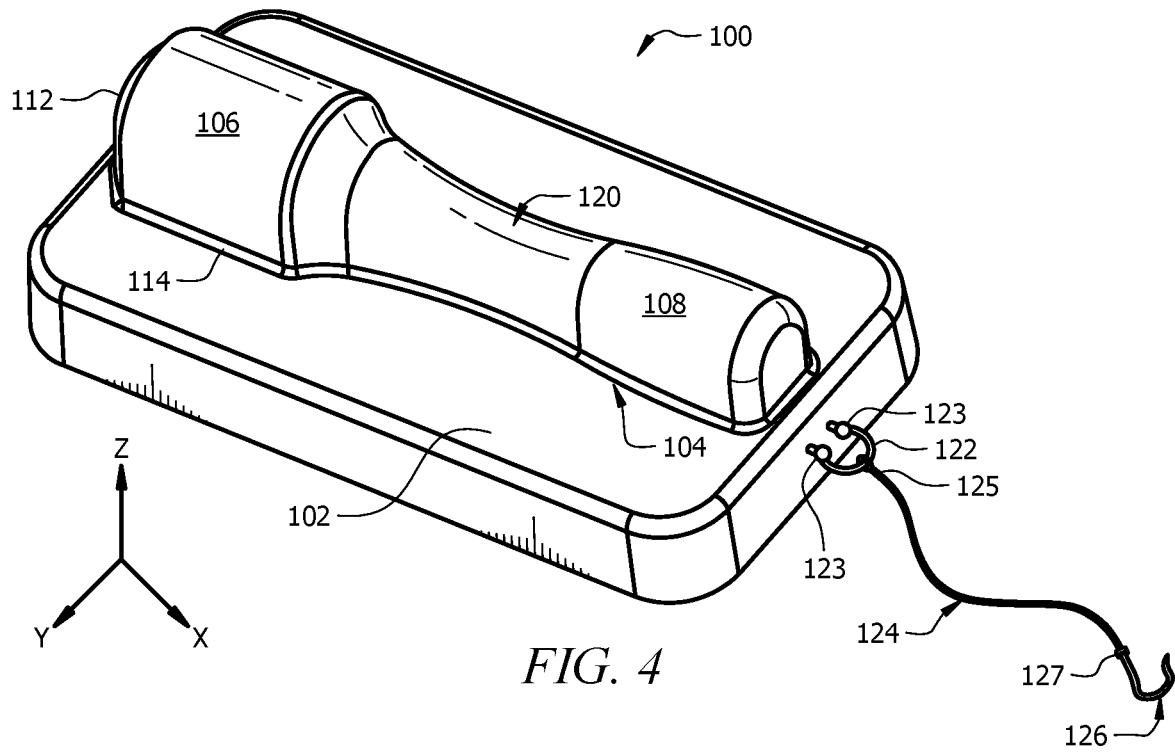
FIG. 4 is a schematic illustration of a nasal cast bender with a line and a hook in accordance with embodiments of the disclosure where contour lines are included for reference.

In another embodiment, as shown in FIG. 4, an eyelet 122 may be attached to the base 102 by any suitable means, such as, for example, by being inserted through the holes 123 of the base 102. The holes 123 may be positioned along any part of the base 102. Attached to the eyelet 122 may be a line 124 (e.g., line 124 may comprise a chain, rope, tube, etc.). The hook 126 may be attached to the distal end 127 (distal relative to the eyelet 122) of the line 124, whereas, the proximal end 125 (proximal relative to the eyelet 122) of the line 124 may be attached to the eyelet 122. The inclusion of the holes 123, the line 124, and the hook 126 may allow the nasal cast bender 100 to be utilized as a weighted retractor. That is, during rhinoplasty, a surgeon may make incisions within each nostril and/or the base of the nose in order to separate nasal skin and/or soft tissue (nasal tissue) from the osseous and cartilaginous structures. The surgeon may then pull back or peel the nasal skin and/or the soft tissue away from the osseous and cartilaginous structures and towards the patient's forehead. Instead of a surgical assistant holding this nasal skin and/or soft tissue back while the surgeon reshapes the osseous and cartilaginous structures, the hook 126 may be positioned into the nasal skin and/or the soft tissue, thereby attaching to the nasal skin and/or soft tissue. The line 124 may be positioned to traverse the patient's forehead, thereby allowing the base 102 to be suspended below the back of the patient's head. The suspension of the base 102 may allow a holding back or retraction of the nasal skin and/or the soft tissue, while the surgeon operates. This utilization of the nasal cast bender 100 as a weighted retractor may allow a surgical assistant to perform other duties instead of holding the nasal skin and/or soft tissue back from the osseous and cartilaginous structures. That is, the utilization of the nasal cast bender 100 as a weighted retractor may make available resources in the operating room that would otherwise be unavailable.

Figure 5A:
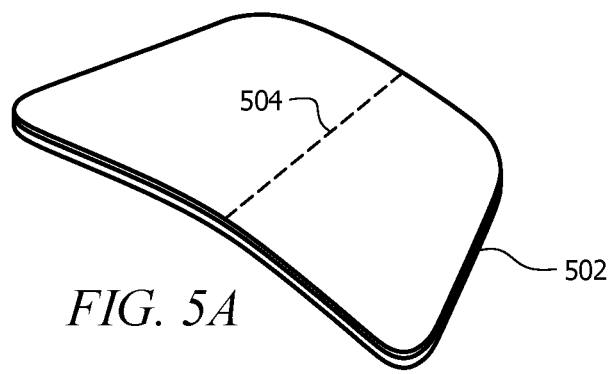
FIGS. 5A and 5B schematically illustrate a nasal cast prior to being shaped and a shaped nasal cast on a patient, respectively.
Figure 5B:
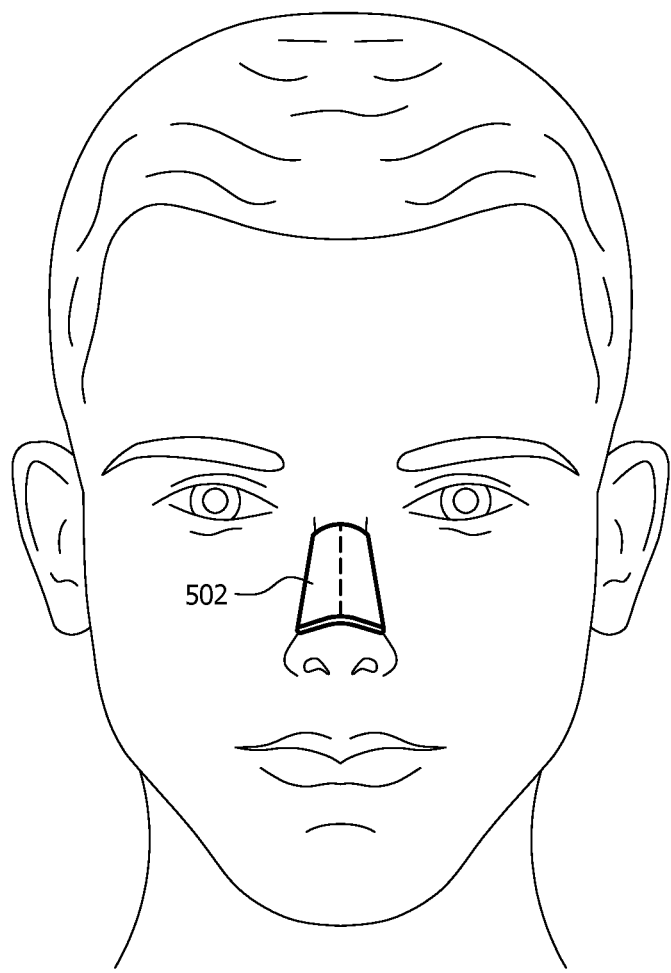

Once a surgery is complete, the nasal cast can be shaped using any of the embodiments of the nasal cast bender 100 described herein. As shown in FIGS. 5A-5B, a nasal cast 502 can have a generally trapezoidal shape and is generally symmetric about a line of symmetry 504, which is relative to the vertical axis extending down a patient's face through a center of the nose. The nasal cast 502 can be made from a deformable material, such as, for example, plastic (e.g., thermoplastic), metal (e.g., aluminum), or combinations thereof. Additional layers may also be present above, below, or around the deformable material to provide airflow, cushioning, or the like when used on the patient. The nasal cast 502 may generally be supplied as a flat or planar device to be shaped to fit a specific patient during a surgery. As described herein, the nasal cast bender 100 can be used to aid in shaping the nasal cast 502. As shown in FIG. 5B, the nasal cast 502 can be disposed over the nose of a patient in a bent or shaped configuration during the surgery. The shaped nasal cast 502 can be placed over the bridge of the nose as shown in FIG. 5B during the surgery to remain in position during the healing process.

With reference to FIGS. 1 through 5B, operation of nasal cast bender 100 may be described as follows. During rhinoplasty, a surgeon may provide (e.g., make available for use during surgery) the nasal cast bender 100. The surgeon may then make incisions within each nostril and/or the base of the nose in order to separate nasal skin and/or soft tissue from the osseous and cartilaginous structures. The surgeon may then pull back or peel the nasal skin and/or soft tissue away from the osseous and cartilaginous structures and towards the patient's forehead. As described above, the nasal cast bender 100 may hold the nasal skin and soft tissue back while the surgeon reshapes the osseous and cartilaginous structures, as desired. After the reshaping, the nasal skin and/or soft tissue may be pulled/positioned/replaced over the osseous and cartilaginous structures; the hook 126 may be removed from the nasal skin and/or soft tissue, thereby separating nasal cast the bender 100 from the nasal skin and/or soft tissue; and the incisions may be sutured. Then, the surgeon may place the nasal cast bender 100 on a flat surface (e.g., a table) in order to utilize the nasal cast bender 100 to shape an external nasal cast 502. The surgeon may grasp the handle 106 for stability, when present, and then press, bend, and/or slide the external nasal cast 502 along the bending surface portion 108, thereby shaping the external nasal cast 502 to desired specifications (e.g., degree of bending of the external nasal cast, positioning of any bends in the external nasal cast, symmetry of the bent cast). The surgeon may symmetrically shape the external nasal cast 502 to allow the reconstructed nose to heal symmetrically relative to a vertical axis extending down a patient's face through a center of the reconstructed nose, thereby creating/providing a symmetrical reconstructed nose. The surgeon may apply the external nasal cast 502 to the reconstructed nose in order for the osseous and cartilaginous structures to heal in their reshaped (symmetrical) position. The external nasal cast may remain on the nose for approximately 7 days to allow for sufficient healing. After approximately 7 days, the external nasal cast 502 may be removed. It should be noted that an external nasal cast's symmetry is relative to the vertical axis extending down a patient's face through a center of the reconstructed nose (e.g., along the line of symmetry 504).

Having described various systems and methods, various embodiments can include, but are not limited to:

In a first embodiment, a nasal cast bender may comprise a base; and a protrusion protruding upwards from the base portion, wherein the protrusion comprises a handle and a bending surface comprising a convex profile; wherein the bending surface is configured to shape an external nasal cast.

A second embodiment may include the nasal cast bender of the first embodiment, wherein the bending surface is tapered.

A third embodiment may include the nasal cast bender of the first or second embodiment, wherein the handle comprises a convex profile.

A fourth embodiment may include the nasal cast bender of any of the preceding embodiments, wherein a circumference of the handle is greater than a circumference of the bending surface.

A fifth embodiment may include the nasal cast bender of any of the preceding embodiments, wherein the bending surface comprises a smooth texture.

A sixth embodiment may include the nasal cast bender of any of the preceding embodiments, wherein the nasal cast bender is 3D printed as a single piece.

A seventh embodiment may include the nasal cast bender of any of the preceding embodiments, wherein the nasal cast bender is made from plastic, metal, or combinations thereof.

An eighth embodiment may include the nasal cast bender of any of the preceding embodiments, wherein the nasal cast bender is hollow.

A ninth embodiment may include the nasal cast bender of any of the first through seventh embodiments, wherein the nasal cast bender is solid.

A tenth embodiment may include the nasal cast bender of any of the preceding embodiments, wherein the bending surface is symmetrical relative to a vertical axis extending from an apex of the bending surface through a center of the bending surface.

An eleventh embodiment may include the nasal cast bender of any of the preceding embodiments, wherein the handle is symmetrical relative to a vertical axis extending from an apex of the handle through a center of the handle.

In a twelfth embodiment, a nasal cast bender may comprise a base; a protrusion protruding upwards from the base portion, wherein the protrusion comprises a handle and a bending surface comprising a convex profile; and a line extending from the base to a hook; wherein the bending surface is configured to shape an external nasal cast.

A thirteenth embodiment may include the nasal cast bender of the twelfth embodiment, wherein the hook is configured to attach to nasal skin.

A fourteenth embodiment may include the nasal cast bender of the twelfth or thirteenth embodiment, wherein the line comprises a chain.

A fifteenth embodiment may include the nasal cast bender of any one of the twelfth through fourteenth embodiments, wherein the base comprises an eyelet.

A sixteenth embodiment may include the nasal cast bender of any one of the twelfth through fifteenth embodiments, wherein the line is attached to the eyelet.

In a seventeenth embodiment, a method for shaping an external nasal cast, the method may comprise providing a nasal cast bender, wherein the nasal cast bender comprises: a base; and a protrusion protruding upwards from the base portion, wherein the protrusion comprises a handle and a bending surface comprising a convex profile; bending, sliding, and/or pressing the external nasal cast along the bending surface, thereby shaping the external nasal cast.

An eighteenth embodiment may include the method of the seventeenth embodiment, further comprising applying the external nasal cast to a reconstructed nose.

In a nineteenth embodiment, a method for retracting nasal skin and/or soft tissue, the method may comprise providing a nasal cast bender, wherein the nasal cast bender comprises: a base; a protrusion protruding upwards from the base portion, wherein the protrusion comprises a handle and a bending surface comprising a convex profile; and a line extending from the base to a hook; making incisions within each nostril and/or a base of a nose; separating the nasal skin and/or the soft tissue from osseous and cartilaginous structures; attaching the hook to the nasal skin and/or the soft tissue; peeling the nasal skin and/or the soft tissue towards a forehead of a patient; traversing the forehead with the line; and suspending the nasal cast bender below a head of the patient with the line, thereby retracting the nasal skin and/or the soft tissue.

A twentieth embodiment may include the method of the nineteenth embodiment, further comprising removing the hook; positioning the nasal skin over the osseous and cartilaginous structures; and suturing the incisions.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A nasal cast bender comprising:
a base portion, wherein the base portion comprises a flat top and a flat bottom; and
a protrusion protruding upwards from the flat top of the base portion, wherein the protrusion comprises a handle and a bending surface, wherein the bending surface comprises a varying radius along a length of the bending surface, wherein the bending surface protrudes upwards from the flat top of the base portion, wherein the bending surface forms a convex profile protruding upwards from the flat top of the base portion, wherein a radius of the bending surface decreases from a radius of the handle between the handle and a midpoint of the bending surface, and wherein the radius of the bending surface increases from the midpoint to an end opposite the handle;
wherein the bending surface is configured to shape an external nasal cast.

2. The nasal cast bender of claim 1, wherein the bending surface is tapered along the length of at least a portion of the bending surface.

3. The nasal cast bender of claim 2, wherein the handle comprises a convex profile.

4. The nasal cast bender of claim 3, wherein a circumference of the handle is greater than a circumference of the bending surface.

5. The nasal cast bender of claim 4, wherein the bending surface comprises a smooth texture.

6. The nasal cast bender of claim 5, wherein the nasal cast bender is 3D printed and formed as a single, integral piece.

7. The nasal cast bender of claim 6, wherein the nasal cast bender is made from a material comprising plastic, metal, or combinations thereof, wherein a surface of the nasal cast bender has a non-porous surface, and wherein the material is configured to be autoclaved.

8. The nasal cast bender of claim 7, wherein the nasal cast bender is hollow.

9. The nasal cast bender of claim 1, wherein the nasal cast bender is solid.

10. The nasal cast bender of claim 1, wherein the bending surface is symmetrical relative to a vertical axis extending from an apex of the bending surface through a center of the bending surface.

11. The nasal cast bender of claim 1, wherein the handle is symmetrical relative to a vertical axis extending from an apex of the handle through a center of the handle.

12. A nasal cast bender comprising:
a base portion, wherein the base portion comprises a flat top;
a protrusion protruding upwards from the flat top of the base portion, wherein the protrusion comprises a bending surface, wherein the bending surface comprises a varying radius along a length of the bending surface, wherein the bending surface protrudes upwards from the flat top of the base portion, and wherein the bending surface forms a convex profile in the form of an upside down U protruding upwards from the flat top of the base portion; and
a line extending from the base portion to a hook;
wherein the bending surface is configured to shape an external nasal cast.

13. The nasal cast bender of claim 12, wherein the hook is configured to attach to nasal skin.

14. The nasal cast bender of claim 13, wherein the line comprises a chain.

15. The nasal cast bender of claim 14, wherein the base portion comprises an eyelet.

16. The nasal cast bender of claim 15, wherein the line is attached to the eyelet.

17. A method for shaping an external nasal cast, the method comprising:
providing a nasal cast bender, wherein the nasal cast bender comprises:
a base portion, wherein the base portion comprises a flat top; and
a protrusion protruding upwards from the flat top of the base portion, wherein the protrusion comprises a bending surface, wherein the bending surface protrudes upwards directly from the flat top of the base portion, and wherein the bending surface forms a convex profile in the form of an upside down U protruding upwards from the flat top of the base portion;
bending, sliding, and/or pressing the external nasal cast along the bending surface; and
shaping the external nasal cast based on the bending, sliding, and/or pressing.

18. The method of claim 17, further comprising applying the external nasal cast to a reconstructed nose.

19. A method for retracting nasal skin and/or soft tissue, the method comprising:
providing a nasal cast bender, wherein the nasal cast bender comprises:
a base portion, wherein the base portion comprises a top and a bottom;
a protrusion protruding upwards from the top of the base portion, wherein the protrusion comprises a bending surface, wherein the bending surface comprises a varying radius along a length of the bending surface, wherein the bending surface protrudes upwards directly from the top of the base portion, and wherein the bending surface forms a convex profile in the form of an upside down U protruding upwards from the flat top of the base portion; and
a line extending from the base portion to a hook;
separating a nasal skin and/or soft tissue from osseous and cartilaginous structures;
peeling the nasal skin and/or the soft tissue towards a forehead of a patient;
attaching the hook to the nasal skin and/or the soft tissue;
traversing the forehead with the line;
suspending the nasal cast bender past the forehead of the patient with the line; and retaining the nasal skin and/or the soft tissue separated from the osseous and cartilaginous structures using the nasal cast bender suspended past the forehead of the patient.

20. The method of claim 19, further comprising:

removing the hook;

positioning the nasal skin over the osseous and cartilaginous structures; and suturing the incisions.

\* \* \* \* \*